(12) United States Patent
Kuo et al.

(10) Patent No.: US 10,564,119 B2
(45) Date of Patent: *Feb. 18, 2020

(54) DIRECT SEQUENCING DEVICE WITH A TOP-BOTTOM ELECTRODE PAIR

(71) Applicant: SEAGATE TECHNOLOGY LLC, Cupertino, CA (US)

(72) Inventors: David S. Kuo, Palo Alto, CA (US); ShuaiGang Xiao, Fremont, CA (US); Kim Yang Lee, Fremont, CA (US); Xiaomin Yang, Livermore, CA (US); Koichi Wago, Sunnyvale, CA (US); Thomas Young Chang, Menlo Park, CA (US)

(73) Assignee: SEAGATE TECHNOLOGY LLC, Cupertino, CA (US)

( * ) Notice: Subject to any disclaimer, the term of this patent is extended or adjusted under 35 U.S.C. 154(b) by 63 days.

This patent is subject to a terminal disclaimer.

(21) Appl. No.: 15/886,685

(22) Filed: Feb. 1, 2018

(65) Prior Publication Data

US 2018/0217084 A1 Aug. 2, 2018

Related U.S. Application Data

(60) Provisional application No. 62/453,329, filed on Feb. 1, 2017.

(51) Int. Cl.
| | |
|---|---|
| *G01N 27/327* | (2006.01) |
| *G01N 33/487* | (2006.01) |
| *B82Y 40/00* | (2011.01) |
| *G01N 33/543* | (2006.01) |
| *C12Q 1/6869* | (2018.01) |
| *B82Y 5/00* | (2011.01) |

(52) U.S. Cl.
CPC .......... *G01N 27/3278* (2013.01); *B82Y 40/00* (2013.01); *G01N 33/48721* (2013.01); *G01N 33/5438* (2013.01); *B82Y 5/00* (2013.01); *C12Q 1/6869* (2013.01)

(58) Field of Classification Search
CPC .......................... G01N 33/48721; B82Y 40/00
See application file for complete search history.

(56) References Cited

U.S. PATENT DOCUMENTS

| | | | |
|---|---|---|---|
| 9,410,923 B2 | 8/2016 | Sauer et al. | |
| 2010/0267158 A1* | 10/2010 | Chou | B01L 3/502761 436/94 |
| 2014/0151228 A1* | 6/2014 | Royyuru | B82Y 15/00 204/451 |
| 2017/0253479 A1* | 9/2017 | Nikoobakht, IV | B82B 3/0019 |

OTHER PUBLICATIONS

Duan et al., Review article: Fabrication of nanofluidic devices, Biomicrofluidics 7, 026501 (2013) (Year: 2013).*

(Continued)

*Primary Examiner* — Alexander S Noguerola
(74) *Attorney, Agent, or Firm* — Holzer Patel Drennan (57) ABSTRACT

A DNA sequencing device includes a first layer having a nanochannel formed therein, and a pair of electrodes arranged vertically relative to each other and spaced apart to define an electrode gap. The electrode gap is exposed in the nanochannel, and the electrode gap is in the range of about 0.3 nm to about 2 nm.

18 Claims, 7 Drawing Sheets

(56) References Cited

OTHER PUBLICATIONS

Di Ventra, Massimiliano, et al., "Decoding DNA, RNA and peptides with quantum tunneling," Nature Nanotechnology, vol. 11, Feb. 2016, pp. 117-126.
Feng, Yanxiao, et al., "Nanopore-based Fourth-generation DNA Sequencing Technology," Genomics Proteomics Bioinformatics, 13 (2015), pp. 4-16.
Ivanov, A.P., et al., "DNA Tunneling Detector Embedded in a Nanopore," Nano Letters, 2011, 11, pp. 279-285.
Ke, Rongqin, et al., "Fourth Generation of Next-Generation Sequencing Technologies: Promise and Consequences," Human Mutation, vol. 37, No. 12, 2016, pp. 1363-1367.
Kulski, Jerzy K., "Next-Generation Sequencing—An Overview of the History, Tools, and 'Omic' Applications," http://dx.doi.org/10.5772/61964, 59 pages.

* cited by examiner

DIRECT SEQUENCING DEVICE WITH A TOP-BOTTOM ELECTRODE PAIR

RELATED APPLICATIONS

This application claims the benefit of the filing date of U.S. Provisional Application No. 62/453,329, filed on 1 Feb. 2017, and entitled DIRECT SEQUENCING DEVICE WITH A TOP-BOTTOM ELECTRODE PAIR, the disclosure of which is incorporated in its entirety by this reference.

SUMMARY

The present disclosure relates to DNA sequencing devices, methods of fabricating aspects of a DNA sequencing device, and related DNA sequencing methods using such devices. One aspect of the present disclosure relates to a DNA sequencing device that includes a first layer having a nanochannel formed therein, and a pair of electrodes arranged vertically relative to each other and spaced apart to define an electrode gap. The electrode gap is exposed in the nanochannel, and the electrode gap is in the range of about 0.3 nm to about 2 nm.

A width of nanochannel may be no greater than about 100 nm. The gap may have a width equal to a width of the nanochannel. The gap may be no greater than about 2 nm. The gap may have a width that is greater than a width of the nanochannel. The electrodes may each comprise a metal material. The electrodes may be embedded in the first layer, and the first layer may be formed on a substrate.

Another aspect of the present disclosure relates to a method of forming a nanochannel device for DNA sequencing. The method includes depositing a first electrode layer on a substrate, depositing an insulator layer on the first electrode layer, depositing a second electrode layer on the insulator layer, patterning the first and second electrode layers and the insulator layer to form top and bottom electrodes spaced apart by the insulator layer, applying a coating to the substrate to embed the top and bottom electrodes, etching back the coating to expose the top electrode, patterning a nanochannel in the coating, and removing the insulator layer between the top and bottom electrodes to form a gap, the gap being exposed within the nanochannel.

Applying the coating may include applying the coating as a spin on glass (SOG) or a spin-on/dispensed polymer coating. The method may include providing a base insulator layer on the substrate, the first electrode layer being formed on the base insulator layer. Patterning the nanochannel may include forming the nanochannel to have a width no greater than about 100 nm. The insulator layer may have a thickness of no greater than about 10 nm, and the gap may be defined by the thickness of the insulator layer. The gap may be in the range of about 0.3 nm to about 2 nm. The gap has a width, and the gap width may be greater than a width of the nanochannel. The method may include covering the coating and electrodes with a polydimethylsiloxane (PDMS) material.

A further aspect of the present disclosure relates to a method of DNA sequencing. The method includes providing a DNA sequencing device having a first layer, a nanochannel formed in the first layer, a pair of electrodes arranged vertically relative to each other and spaced apart to define an electrode gap, the electrode gap being exposed in the nanochannel, the electrode gap being in the range of about 0.3 nm to about 2 nm. The method also includes passing a DNA strand through the nanochannel and the gap, detecting with the electrodes an electronic signal associated with individual nucleotides of the DNA strand as the DNA strand passes through the gap, and determining a sequence of the nucleotides based on the electronic signals.

Passing the DNA strand through the nanochannel and the gap may include moving the DNA strand using electrophoresis. The method may include comparing the electronic signals to stored values for each nucleotide types. The DNA sequencing device may further include a controller operable to receive the electronic signals and control operation of the electrodes. The method may include displaying the DNA sequence on a display device.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

Despite considerable efforts, DNA sequencing today still suffers from high costs and low speeds. To address these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

Direct measure of individual nucleotides of long DNA strands rapidly and with low cost is one goal of DNA sequencing. Among these options, nanopore- and nanochannel-based approaches that measure a transverse signal across individual nucleotides have emerged as a promising approach. The general approach involves electrically driving DNA and RNA strands through a nanopore or narrow channel via ionic flow or driven by a pressure gradient. As the strand passes a high resolution sensor embedded inside the channel (e.g., a nanoelectrode), the high spatial resolution sensor measures the unique properties of the individual nucleotides (A,T,C,G). One type of sensor would consist of a conductive electrode that measures the unique tunneling currents associated with the nucleotide, thereby identifying and resolving the four unique nucleotide types.

However, there are several significant challenges associated with the fabrication of such devices at relatively low cost that can spatially resolve individual nucleotides of each strand, wherein nucleotides are on the order of about 1 nm is size in a transverse direction. One challenge is the ability to fabricate a channel width on the order of about 1 nm to about 100 nm with accuracy and repeatability to obtain tunneling current that is exponential verses distance. Such a channel or pore is sometimes referred to as a nanochannel or nanopore. For example, the signal tunneling current would reduce by a factor of about 1000× if spacing is increased between electrode and base molecule by only about 0.5 nm. A second challenge relates to fabrication of a sensor or nanoelectrode that is on the order of about 1 nm in spacing between the electrodes in order to resolve and detect individual nucleotides (e.g., A,T,C,G) in the DNA strand.

A relatively fast and low-cost genome (DNA), transcriptome (RNA) and proteome (all proteins) sequencing method could lead to the development of personalized medicine (e.g., the ability to target drugs and medical treatments specially to an individual). However, to fabricate a nanochannel for single molecular DNA sequencing is still technically challenging due to the extremely small dimensions involved with the devices used to conduct the sequencing. The devices and methods disclosed herein address at least some of these challenges.

To improve DNA sequencing throughput and lower the cost, direct-reading sequencing device like nanochannel devices based on, for example, (1) semiconductor nanochannel, and (2) transverse electron current measurement may be highly desirable.

A nanochannel structure with a pair of transverse electrodes can be fabricated using conventional nanofabrication processes. A limitation of this structure is the relatively wide nanogap between two electrodes defined by, for example, lithography. The nanogap is typically in the range of 10 nm to about 30 nm. Ideally a small nanogap between two electrodes on the order of about 0.3 nm and about 2 nm (more particularly on the order of about 1 nm) is preferred to enhance the signal-to-noise ratio during transverse current detection due to the ultra-small diameter of DNA single strand (~1 nm). The present disclosure relates to a new design for a tunneling electrode for a DNA sequencing device, the tunneling electrode having two transverse electrode member having a uniform, ultra-small nanogap on the order of about 1 nm (e.g., in the range of about 0.3 nm to about 2 nm). A fabrication process flow to create at least one of the electrode members having a wedge-shape or tapered shape is described as well.

The present disclosure generally relates to DNA sequencing, and more particularly relates to DNA sequencing devices having nanochannels and nanoelectrodes, and related methods of fabricating such devices. An example DNA sequencing device includes a substrate, an in-plane nanochannel positioned on the substrate, and a top-bottom pair of electrodes extending through the nanochannel and having a gap formed there between that aligns with the nanochannel. The present disclosure may also relate to DNA sequencing using such devices.

The present disclosure also relates to methods for fabricating a DNA nanochannel with a very small tunneling electrode gap (e.g., in the range of about 0.3 nm to about 2 nm), as well as the resultant DNA nanochannel itself and the electrode members of the tunneling electrode (also referred to as a nanoelectrode). The disclosed methods may include fabricating the gap using thin film deposition of an insulator layer between a bottom electrode layer (e.g., metal layer) and a top electrode layer (e.g., metal layer). The two electrode layers and associate pads may be accessible for transverse current measurement.

The present disclosure also relates to a DNA sequencing device having a width no greater than about 100 nm. Alternatively, a width of the nanochannel may be no greater than about 1 nm to 100 nm. The gap between electrodes may be no greater than about 2 nm. The nanochannel may be formed, for example, in a spin-on-glass (SOG) or a spin-on/dispensed polymer layer. The electrodes may include a metal material. The gap may have a width that is greater than a width of the nanochannel.

Another aspect of the present disclosure relates to a method of forming a nanochannel device for DNA sequencing. The method includes depositing a first electrode layer on a substrate, depositing an insulator layer on the first electrode layer, depositing a second electrode layer on the insulator layer, patterning the first and second electrode layers and the insulator layer to form top and bottom electrodes spaced apart by the insulator layer, applying a spin-on-glass (SOG) or a spin-on/dispensed polymer coating to the substrate, etching back the SOG/polymer coating to expose the top electrode, patterning a nanochannel in the SOG/polymer coating, and removing the insulator layer between the top and bottom electrodes to form a gap, the gap being exposed within the nanochannel.

The method may further comprise providing a base insulator layer on the substrate, wherein the first electrode layer is positioned on the base insulator layer. The gap may be no greater than about 2 nm. The gap may be in the range of about 0.3 nm to about 2 nm. The gap may have a width that is less than a width of the nanochannel. In some embodiments, the gap may have a width that is equal to a width of the nanochannel.

Figure 1A:
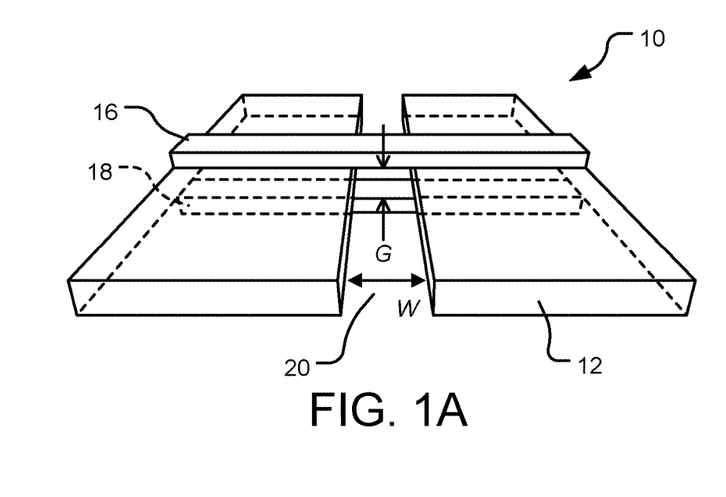
FIG. 1A shows a DNA sequencing device with an in-plane nanochannel having a top-bottom electrode pair in accordance with the present disclosure.
Figure 1B:
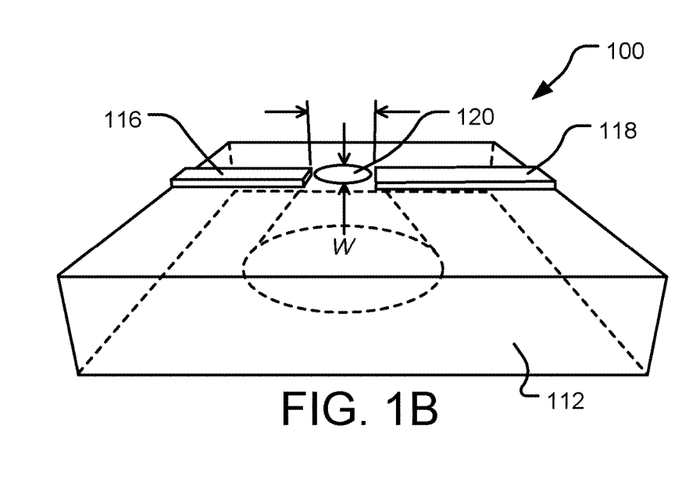
FIG. 1B shows a DNA sequencing device with an out-of-plane nanopore in accordance with the present disclosure.
Figure 1C:
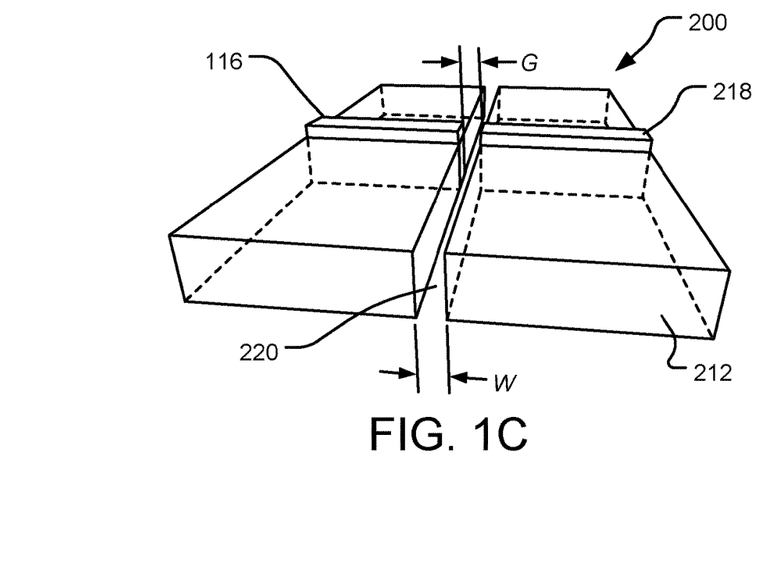
FIG. 1C shows a DNA sequencing device with an in-plane nanochannel having a side-by-side electrode pair in accordance with the present disclosure.

FIGS. 1A-1C show several possible DNA sequencing device designs, each of which integrate a nanochannel or nanopore structure and a pair of transverse electrodes integrated therein. In each of the embodiments shown in 1A-1C, the transverse electrodes are exposed within the nanochannel or nanopore structure, and are spaced apart a distance to define a gap G, through which a DNA strand passes. The transverse electrodes generate an electronic signal associated with each nucleotide of the DNA strand. These measured electronic signals are then used to determine a sequence of the nucleotides on the DNA strand.

FIG. 1A illustrates a DNA sequencing device 10 having a substrate 12 within which a nanochannel 20 is formed. First and second electrodes 16, 18 are arranged vertically or stacked, one above the other, and spaced apart to define a gap G. At least a portion of the gap G is exposed within the nanochannel 20. The nanochannel has a width W.

FIG. 1B illustrates a DNA sequencing device 100 having a substrate 112 and a nanopore structure 120 formed therein. First and second electrodes 116, 118 are arranged end-to-end, and typically within a common horizontal plane. The electrodes 116, 118 are spaced apart a distance that defines a gap G. The gap G typically is less than a minimum width W at an entry point to the nanopore 120.

FIG. 1C illustrates a DNA sequencing device 200 having a substrate 212 with a nanochannel 220 formed therein. First and second electrodes 216, 218 are arranged end-to-end typically within a common horizontal and/or vertical plane. The electrodes 216, 218 are spaced apart a distance defining a gap G. The gap G is typically less than a width W of the nanochannel 220.

Although the present disclosure focuses primarily on the DNA sequencing device 10 shown in FIG. 1A, the principles disclosed herein may be generally applicable to the designs shown in FIGS. 1B and 1C, and other nanochannel and/or nanopore structures for use in DNA sequencing devices and systems.

Figure 2A:
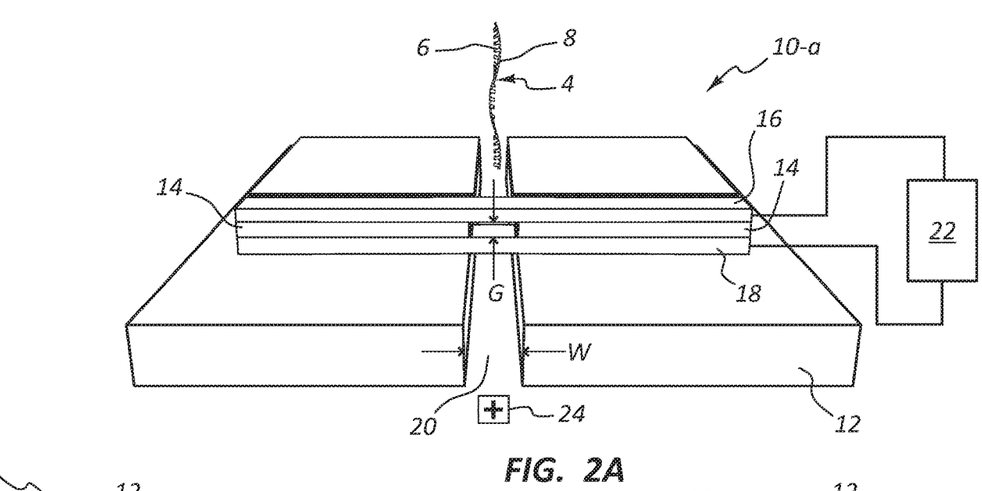
FIG. 2A shows a top-bottom electrode pair in accordance with the present disclosure.
Figure 2B:
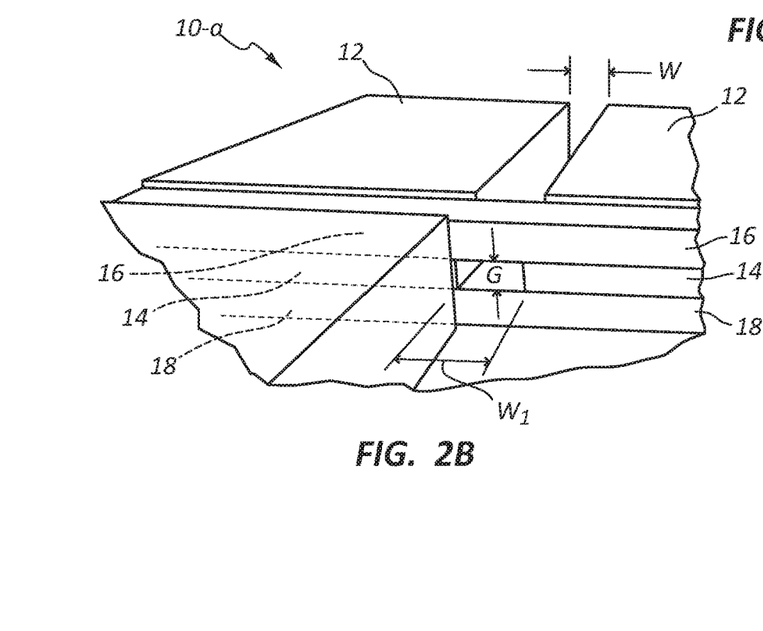
FIG. 2B shows a top-bottom electrode pair with normal channel width in accordance with the present disclosure.

FIGS. 2A and 2B illustrate another example DNA sequencing device 10-$a$ having a similar top/bottom electrode pair design as shown in FIG. 1A. The device 10-$a$ includes a substrate 12, first and second electrodes 16, 18 arranged vertically relative to each other, an insulator 14 positioned there between, and a nanochannel 20 formed in the substrate 12. The first and second electrodes 16, 18 are spaced apart to define a gap G that is exposed within the nanochannel 20. A DNA strand 4 having a plurality of nucleotides 6 mounted to a backbone 8, is drawn through the nanochannel 20 and gap G using, for example, electrophoresis operable in part using an energy source 24.

Figure 2C:
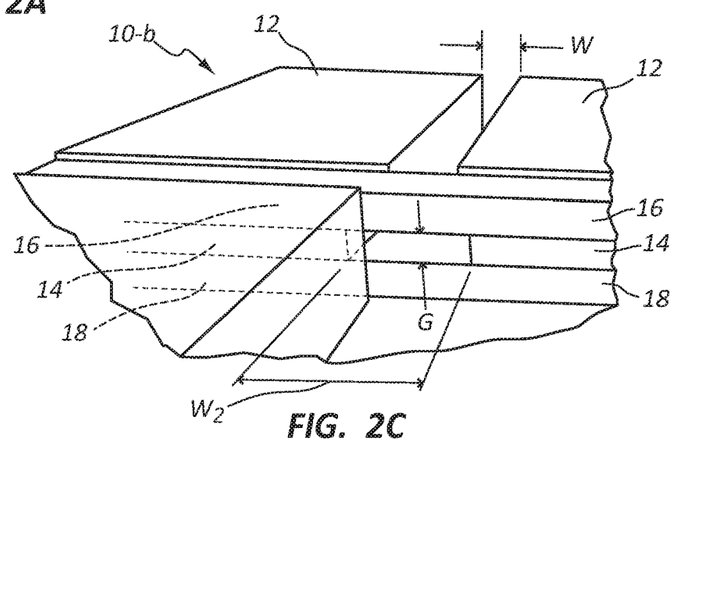
FIG. 2C shows a top-bottom electrode pair with wide channel width in accordance with the present disclosure.

FIG. 2B illustrates the gap G of DNA sequencing device 10-$a$ having a width $W_1$. The width $W_1$ may be substantially the same size as the width W of the nanochannel 20. FIG. 2C illustrates an alternative version of a DNA sequencing device 10-$b$ in which the width $W_2$ of the gap G is greater than the width W of the nanochannel 20. The width of the gap G may vary depending upon a variety of factors including, for example, fabrication techniques used, insulative material for the insulator 14, performance characteristics of the electrodes 16, 18, and the like.

The gap G typically is in the range of about 0.3 nm to about 2 nm, and more particularly no greater than about 1 nm. The width W of the nanochannel 20 typically is in the range of about 5 nm to about 50 nm, and more particularly about 10 nm to about 30 nm. Typically, the width $W_1$ and/or width $W_2$ of the gap G is equal to or greater than the width W of the nanochannel 20.

The gap G may be controlled at least in part by, for example, thin film deposition of an insulator layer 14 between the first and second electrodes 16, 18 during fabrication. As shown in at least FIG. 2A, portions of the electrodes 16, 18 may be accessible for electronic communication with the controller or pre-amp 22 to provide a transverse current measurement of the DNA strand 4 as it passes through the gap G.

FIGS. 3A-3F illustrate two dimensional (2D) top and side views (1),(2) of a plurality of fabrication steps potentially involved with forming a nanochannel having an integrated top/bottom electrode pair in accordance with the present disclosure. The method steps shown in FIGS. 3A-3F are exemplary only, and other methods may include more or fewer steps using different types of fabrication techniques and/or materials to provide a desired structure and/or function for the resulting DNA sequencing device 10.

Figure 3A:
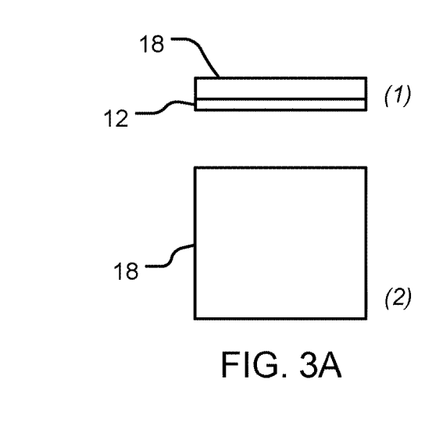
FIGS. 3A-3F show two dimensional (2D) views of steps of a fabrication process for a top-bottom electrode pair in accordance with the present disclosure.
Figure 3B:
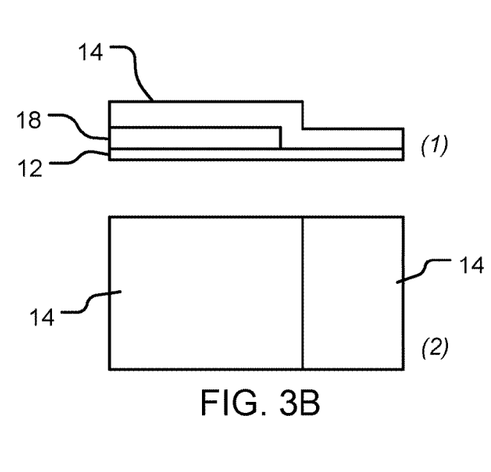
Figure 3C:
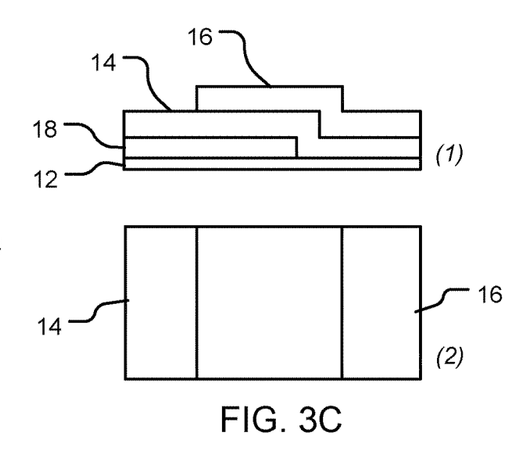

An initial step of forming a first conductive layer 18 on a substrate 12 is shown in FIG. 3A. FIG. 3B illustrates forming an insulator layer 14 (e.g., layer of Carbon material or silicon oxide) deposited on the conductive layer 18. A second conductive layer 16 is then deposited on the insulator layer 14 as shown in FIG. 3C. In some embodiments, the layers 12, 14, 16, 18 may be formed with a step-type structure as shown in the side view of FIG. 3C(1).

Figure 3D:
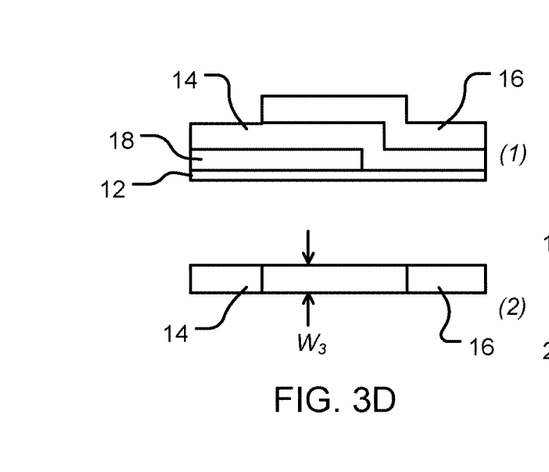
Figure 3E:
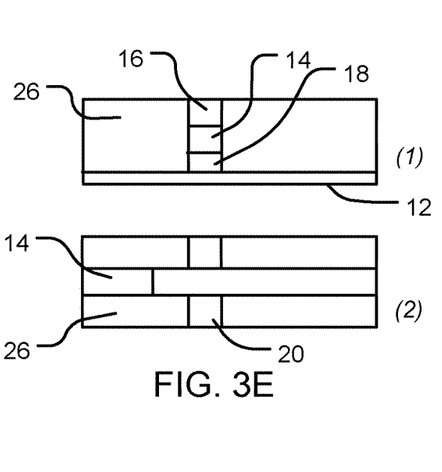

FIG. 3D shows a patterning step to trim the structure of the conductor/insulator/conductor to a width typically in the range of about 5 nm to about 30 nm, and more particularly about 10 nm. Many sizes are possible for the width $W_3$, although the width $W_3$ is typically on the same order of magnitude as the width of the nanochannel and/or size of the gap G. Patterning may be performed to create a nanofluidic duct with imprint, deposition, and/or etching as shown in FIG. 3E, with a resulting nanochannel 20 structure. The deposition may involve depositing a coating layer 26 to at least partially embed or enclose the stack of the conductor 16, insulator 14, and conductor 18. The nanochannel 20 may be formed in the coating layer 26.

Figure 3F:
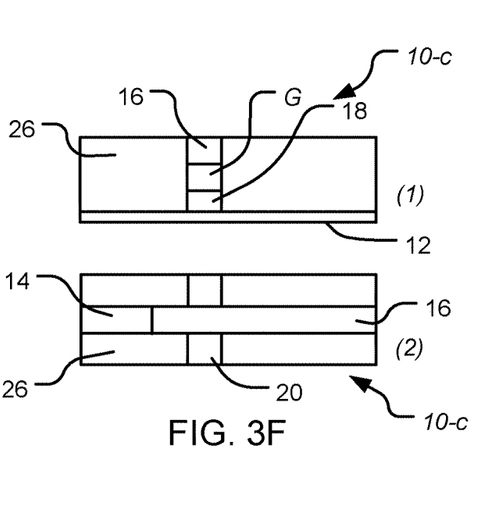

Further etching may be conducted to remove a portion of the insulator 14 between the conductive layers 16, 18 to form a gap G, as shown in FIG. 3F. The resulting gap G is a space between the conductors 16, 18 (also referred to as electrodes 16, 18). The gap G may be exposed within the nanochannel 20. The structures shown in FIG. 3F may be covered with a sealing material such as polydimethylsiloxane (PDMS) using, for example, a spin-coating process. The resulting structure shown in FIG. 3F may be considered a DNA sequencing device 10-$c$, or a portion of a DNA sequencing device.

FIGS. 4A-4G illustrate three-dimensional (3D) views of various fabrication steps involved with forming a DNA sequencing device 10-$d$ having a nanochannel with an integrated top/bottom electrode pair. The fabrication steps shown in FIGS. 4A-4G may overlap or repeat at least some of the fabrication steps shown in FIGS. 3A-3F. The resulting DNA sequencing device 10-$d$ shown in FIG. 4G may have the same or similar features as the DNA sequencing devices 10, 10-a, 10-b and 10-c shown in FIGS. 1A and 2A-3F.

Figure 4A:
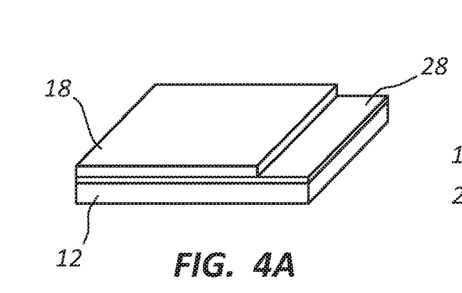
FIGS. 4A-4G show three dimensional (3D) views of steps of a fabrication process of another top-bottom electrode pair in accordance with the present disclosure.
Figure 4B:
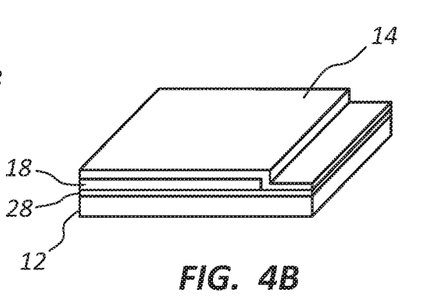

Referring first to FIG. 4A, a substrate 12 has a base insulator layer 28 formed thereon, and a first conductive layer 18 (e.g., a first electrode metal or other conductive material) is formed on a portion of the first insulator layer 28. FIG. 4B shows a second insulator layer 14 formed on the first conductive layer 18. An exposed side or lateral face of the first conductive layer 18 is covered by the insulator layer 14. The insulator layer 14 may extend along an exposed portion of the first insulator layer 28, such as along a top, horizontal surface of the insulator layer 28.

Figure 4C:
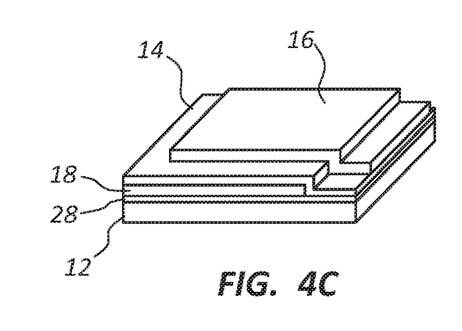

FIG. 4C illustrates a second conductive layer 16 (e.g., a second electrode metal or other conductive material) deposited on the second insulator layer 14. The second conductive layer 16 may cover a exposed side or lateral face of the insulator layer 14, which tracks a shape of the exposed side or lateral face of the first conductive layer 18.

Figure 4D:
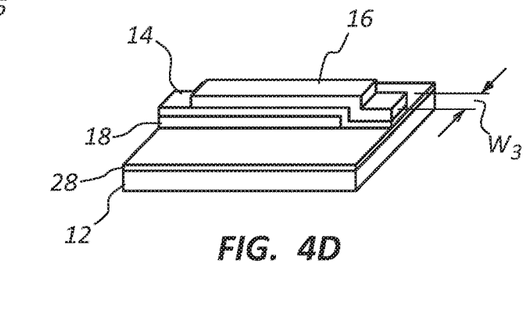

FIG. 4D illustrates patterning of the conductive layers 16, 18 and the insulator layer 14. The patterning may result in a stack of the conductive layers 16, 18 and insulator 14 having a width $W_3$. The width $W_3$ may have a size on the same order of magnitude as, for example, a width of the nanochannel formed in a later step, and/or a size of a gap G between the conductive layers 16, 18 as described with reference to FIG. 4G.

Figure 4E:
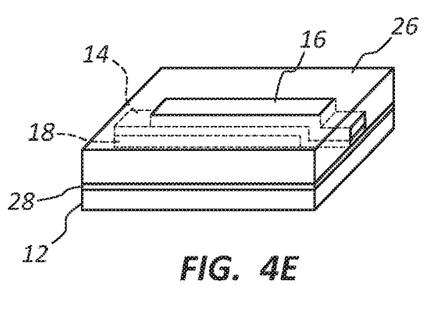

FIG. 4E illustrates formation of a coating layer 26 using, for example, a planarization technique and a spin-on glass (SOG) or a spin-on/dispensed polymer material. The coating layer 26 is then etched back to expose a portion of the second conductive layer 16 (e.g., a top electrode 16).

Figure 4F:
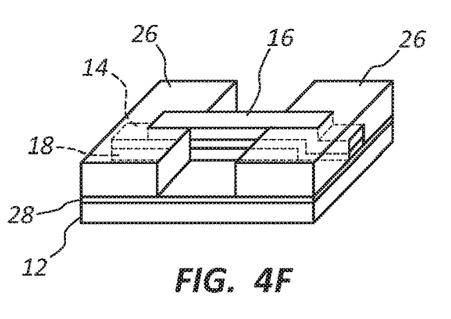

FIG. 4F shows a further fabrication step of channel patterning to form the nanochannel 20 in the coating layer 26. The channel patterning shown in FIG. 4F also exposes portions of the conductive layer 16, 18 on the insulator layer 14. In a further step shown in FIG. 4G, a portion of the insulator 14 is removed from between the conductive layers 16, 18 to form a gap G between the resultant top/bottom electrodes 16, 18.

Figure 4G:
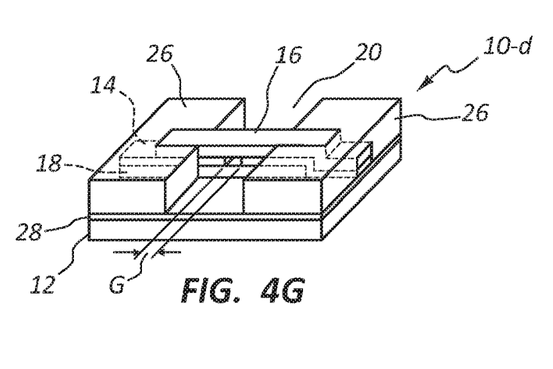
Figure 5:
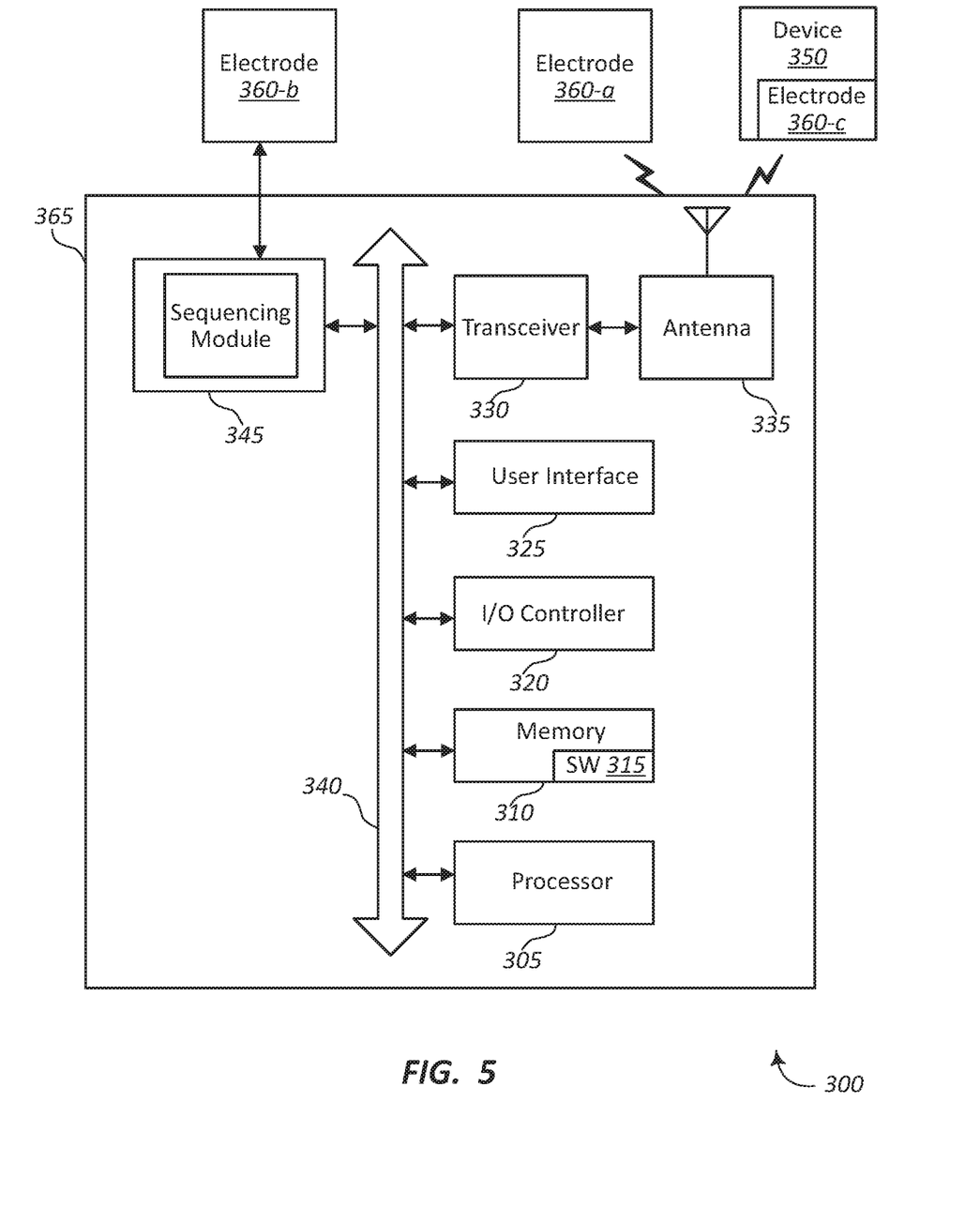
FIG. 5 shows a diagram of a system in accordance with various aspects of this disclosure.

The DNA sequencing device 10-d shown in FIG. 4G may be connected to, for example, a controller or pre-amp, an energy source, and other controls or related components to provide a functional DNA sequencing device and/or system for use in DNA sequencing. FIG. 5 illustrates additional components, systems, and related operability associated with implementing the DNA sequencing devices 10, 100, 200 described herein into a functional device.

The layers shown in FIGS. 1-4G may comprise materials having various desired properties. For example, the substrate 12 may comprise a non-conductive material such as $SiO_2$, or a conductive material such as Si, depending on whether an insulator material is coated on the substrate 12 (e.g., the base insulator layer 28 shown in FIG. 4A). In some embodiments, the coating layer 26 or other layer into which the nanochannel is formed comprises Cr or other non-conductive materials such as Ta and $TiO_2$. The electrodes 16, 18 may comprise a conductive material such as, for example, Au, Pt or Ru. The insulator layer 14 may comprise, for example, C, $SiO_2$, or SiN.

FIG. 5 shows a system 300 for use with the DNA sequencing devices 10, 100, 200 shown in FIGS. 1-4. System 300 may include a control panel 365. Control panel 365 may be equivalent at least in part to the controller 22 described above. Control panel 365 may include sequencing module 345. The sequencing module 345 may provide communications with one or more electrodes 360 directly or via other communication components, such as a transceiver 330 and/or antenna 335. The electrodes 360 may represent one or more of the electrodes 16, 18 or pairs of such electrodes described above with reference to the figures. The sequencing module 345 may perform or control various operations associated with, for example, the electrodes 16, 18, controller 22, energy source 24, or other components of the DNA sequencing devices 10, 100, 200, as described above with reference to FIGS. 1-4.

Control panel 365 may also include a processor module 305, and memory 310 (including software/firmware code (SW) 315), an input/output controller module 320, a user interface module 325, a transceiver module 330, and one or more antennas 335 each of which may communicate, directly or indirectly, with one another (e.g., via one or more buses 340). The transceiver module 330 may communicate bi-directionally, via the one or more antennas 335, wired links, and/or wireless links, with one or more networks or remote devices. For example, the transceiver module 330 may communicate bi-directionally with one or more of device 350 and/or electrodes 360-a, 360-c. The device 350 may be components of the DNA sequencing devices 10 described with reference to FIGS. 1-4, or other devices in communication with the DNA sequencing devices 10. The transceiver 330 may include a modem to modulate the packets and provide the modulated packets to the one or more antennas 335 for transmission, and to demodulate packets received from the one or more antennas 335. In some embodiments (not shown) the transceiver may be communicate bi-directionally with one or more of device 350, remote control device (not shown), and/or electrodes 360-a, 360-c through a hardwired connection without necessarily using antenna 335. While a control panel or a control device (e.g., 365) may include a single antenna 335, the control panel or the control device may also have multiple antennas 335 capable of concurrently transmitting or receiving multiple wired and/or wireless transmissions. In some embodiments, one element of control panel 365 (e.g., one or more antennas 335, transceiver module 330, etc.) may provide a connection using wireless techniques, including digital cellular telephone connection, Cellular Digital Packet Data (CDPD) connection, digital satellite data connection, and/or another connection.

The signals associated with system 300 may include wireless communication signals such as radio frequency, electromagnetics, local area network (LAN), wide area network (WAN), virtual private network (VPN), wireless network (using 802.11, for example), 345 MHz, Z-WAVE®, cellular network (using 3G and/or LTE, for example), and/or other signals. The one or more antennas 335 and/or transceiver module 330 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 335 may receive signals or information specific and/or exclusive to itself. In other embodiments, each antenna 335 may receive signals or information not specific or exclusive to itself.

In some embodiments, one or more electrodes 360 (e.g., angle, velocity, acceleration, force, temperature, etc.) may connect to some element of system 300 via a network using one or more wired and/or wireless connections. In some embodiments, the user interface module 325 may include an audio device, such as an external speaker system, an external display device such as a display screen, and/or an input device (e.g., remote control device interfaced with the user interface module 325 directly and/or through I/O controller module 320).

One or more buses 340 may allow data communication between one or more elements of control panel 365 (e.g., processor module 305, memory 310, I/O controller module 320, user interface module 325, etc.).

The memory 310 may include random access memory (RAM), read only memory (ROM), flash RAM, and/or other types. The memory 310 may store computer-readable, computer-executable software/firmware code 315 including instructions that, when executed, cause the processor module 305 to perform various functions described in this disclosure (e.g., initiating an adjustment of a lighting system, etc.). Alternatively, the software/firmware code 315 may not be directly executable by the processor module 305 but may cause a computer (e.g., when compiled and executed) to perform functions described herein. Alternatively, the computer-readable, computer-executable software/firmware code 315 may not be directly executable by the processor module 305 but may be configured to cause a computer (e.g., when compiled and executed) to perform functions described herein. The processor module 305 may include an intelligent hardware device, e.g., a central processing unit (CPU), a microcontroller, an application-specific integrated circuit (ASIC), etc.

In some embodiments, the memory 310 can contain, among other things, the Basic Input-Output system (BIOS) which may control basic hardware and/or software operation such as the interaction with peripheral components or devices. For example, the resistance module 345, and other modules and operational components of the control panel 365 used to implement the present systems and methods may be stored within the system memory 310. Applications resident with system 300 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 330, one or more antennas 335, etc.).

Many other devices and/or subsystems may be connected to one or may be included as one or more elements of system 300. In some embodiments, all of the elements shown in FIG. 5 need not be present to practice the present systems and methods. The devices and subsystems can be interconnected in different ways from that shown in FIG. 5. In some embodiments, an aspect of some operation of a system, such as that shown in FIG. 5, may be readily known in the art and are not discussed in detail in this application. Code to implement the present disclosure can be stored in a non-transitory computer-readable medium such as one or more of system memory 310 or other memory. The operating system provided on I/O controller module 320 may be iOS®, ANDROID®, MS-DOS®, MS-WINDOWS®, OS/2®, UNIX®, LINUX®, or another known operating system.

The transceiver module 330 may include a modem configured to modulate the packets and provide the modulated packets to the antennas 335 for transmission and/or to demodulate packets received from the antennas 335. While the control panel or control device (e.g., 365) may include a single antenna 335, the control panel or control device (e.g., 365) may have multiple antennas 335 capable of concurrently transmitting and/or receiving multiple wireless transmissions.

Figure 6:
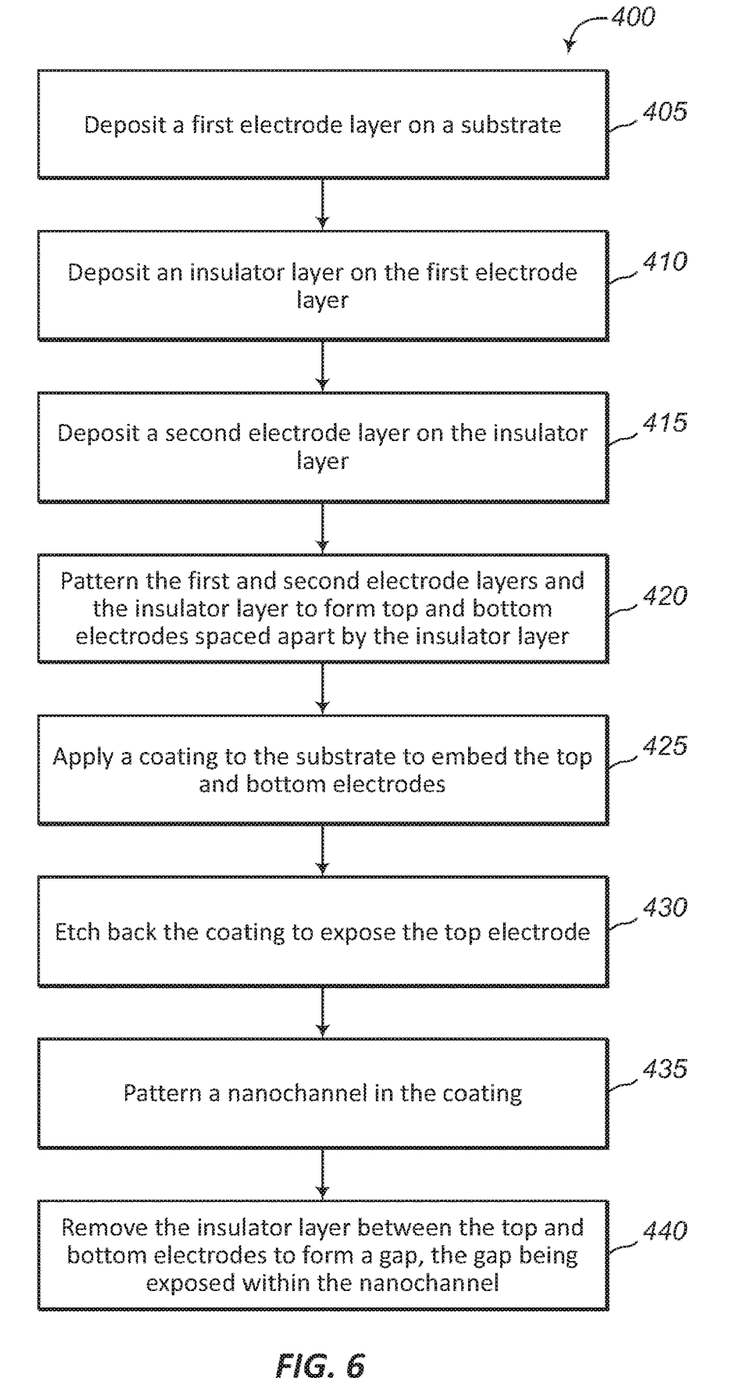
FIG. 6 is a flow diagram showing steps of an example method in accordance with the present disclosure.

FIG. 6 is a flow chart illustrating an example of a method 400 for fabrication of a DNA sequencing device, in accordance with various aspects of the present disclosure. One or more aspects of the method 400 may be implemented in conjunction with the devices 10 of FIGS. 1-4. In some examples, a computing device may execute one or more sets of code to control functional elements of the DNA sequencing devices disclosed herein to perform one or more of the functions described below. Additionally, or alternatively, computing devices and/or storage devices may perform one or more of the functions described below using special-purpose hardware.

The method 400 may include, at block 405, depositing a first electrode layer on a substrate at block 410. The method 400 may include depositing an insulator layer on the first electrode layer. Block 415 includes depositing a second electrode layer on the insulator layer. The electrode layer may also be referred to as a conductive or conductor layer. The block 420 includes patterning the first and second electrode layers and the insulator layer to form top and bottom electrodes spaced apart by the insulator layer. The top and bottom electrodes may be arranged vertically relative to each other. Block 425 includes applying a coating to the substrate and the stack of the top and bottom electrodes with insulator layer to embed the top and bottom electrodes. Block 430 includes etching back the coating to expose the top electrode. Block 435 includes patterning a nanochannel in the coating. Patterning the nanochannel may further include exposing portions of the top and bottom electrodes and the insulator layer. Block 440 includes removing the insulator layer between the top and bottom electrodes along at least a portion of the length of the top and bottom electrodes to form a gap. The gap is exposed within the nanochannel.

The method 400 may also include applying the coating by a spin-on-glass (SOG) or a spin-on/dispensed polymer process. The method 400 may further include providing a base insulator layer on the substrate, and forming the first electrode layer on the base insulator layer. The method 400 may provide patterning of the nanochannel to provide a nanochannel having a width no greater than about 100 nm. Insulator may have a thickness of no greater than about 10 nm, and the gap may be defined by the thickness of the insulator layer. The gap may be in the range of about 0.3 nm to about 2 nm. The gap may have a width, and the gap width may be greater than a width of the nanochannel. The method 400 may further include covering the coating and electrodes with a polydimethylsiloxane (PDMS) material.

Figure 7:
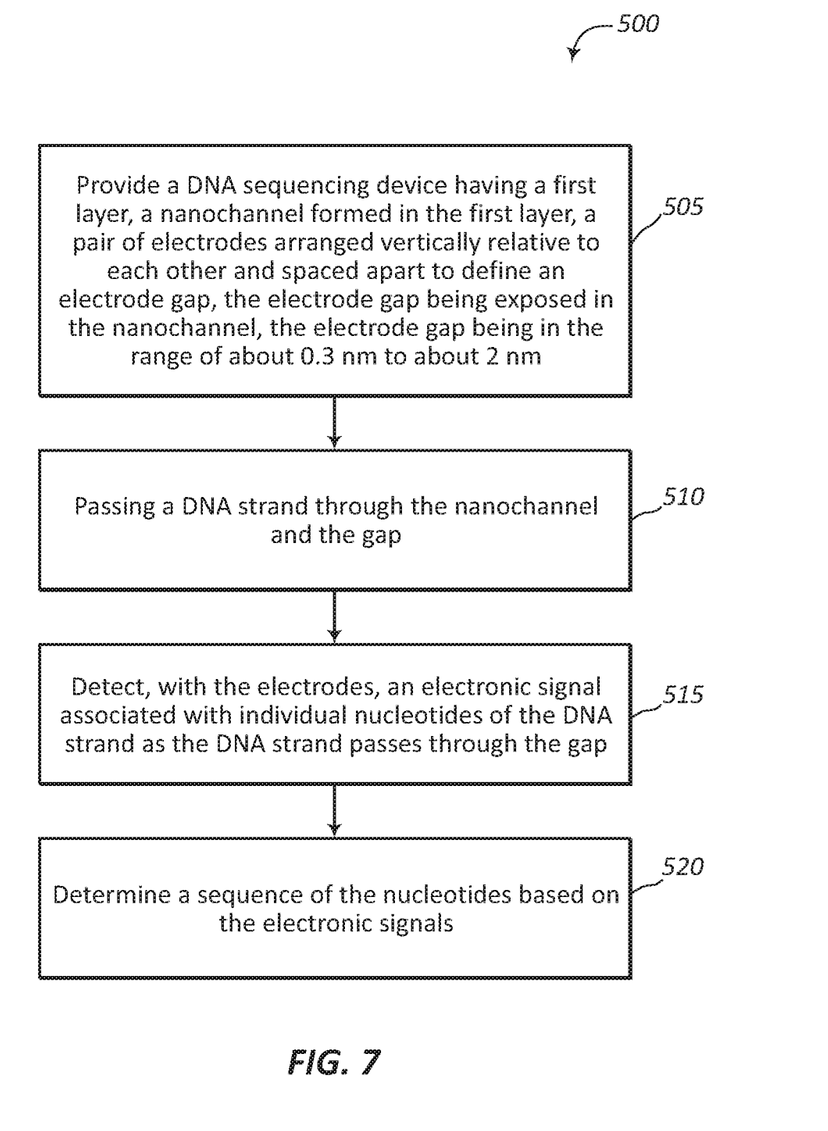
FIG. 7 is a flow diagram showing steps of another example method in accordance with the present disclosure.

FIG. 7 is a flow chart illustrating an example of a method 500 for DNA sequencing, in accordance with the various aspects of the present disclosure. One or more aspects of the method 500 may be implemented in conjunction with the devices 10 described with reference to FIGS. 1-4. In some examples, a computing device may execute one or more sets of code to control functional elements of the DNA sequencing device as disclosed herein to perform one or more of the functions described below. Additionally, or alternatively, computing devices and/or storage devices may perform one or more of the functions described below using special purpose hardware.

The method 500 may include, at block 505, providing a DNA sequencing device having a first layer, a nanochannel formed in the first layer, a pair of electrodes arranged vertically relative to each other and spaced apart to define an electrode gap, the electrode gap being exposed in the nanochannel, and the electrode gap being in the range of about 0.3 nm to about 2 nm. Block 510 includes passing a DNA strand through the nanochannel and the gap. At block 515, the method 500 includes detecting, with the electrodes, an electronic signal associated with the individual nucleotides of the DNA strand as the DNA strand passes through the gap. Block 520 includes determining a sequence of the nucleotides based on the electronic signals that have been detected.

The method 500 may include passing the DNA strand through the nanochannel and the gap using electrophoresis. The method 500 may include comparing the electronic signals to stored values for each nucleotide type. The DNA sequencing device may include a controller operable to receive the electronic signals and control operation of the electrodes. The method 500 may include comparing the electronic signals to stored threshold values associated with each nucleotide type.

In some embodiments, the DNA sequencing devices 10 described herein may be used to collect electronic signals associated with the nucleotides of a DNA strand passing through the gap between top/bottom electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.

U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.

U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.

U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.

U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,393, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2017, and U.S. patent application Ser. No. 15/886,736, titled "METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE," filed on 9 Mar. 2018.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A DNA sequencing device, comprising:
   a first layer having a nanochannel formed therein;
   a pair of electrodes arranged vertically relative to each other and spaced apart to define an electrode gap, the electrode gap being exposed in the nanochannel, the electrode gap having a height measured between the pair of electrodes, the height in the range of about 0.3 nm to about 2 nm, and a width, the width being equal to or greater than a width of the nanochannel.

2. The device of claim 1, wherein a width of nanochannel is no greater than about 100 nm.

3. The device of claim 1, wherein the height of the gap is less than 1 nm.

4. The device of claim 1, wherein the electrodes each comprise a metal material.

5. The device of claim 1, wherein the electrodes are embedded in the first layer, and the first layer is formed on a substrate.

6. A method of forming a nanochannel device for DNA sequencing, the method comprising:
   depositing a first electrode layer on a substrate; depositing an insulator layer on the first electrode layer; depositing a second electrode layer on the insulator layer;
   patterning the first and second electrode layers and the insulator layer to form top and bottom electrodes spaced apart by the insulator layer;
   applying a coating to the substrate to embed the top and bottom electrodes;
   etching back the coating to expose the top electrode;
   patterning a nanochannel in the coating;
   removing the insulator layer between the top and bottom electrodes to form a gap, the gap being exposed within the nanochannel.

7. The method of claim 6, wherein applying the coating includes applying the coating as a spin on glass (SOG) or a spin-on/dispensed polymer coating.

8. The method of claim 6, further comprising providing a base insulator layer on the substrate, the first electrode layer being formed on the base insulator layer.

9. The method of claim 6, wherein patterning the nanochannel includes forming the nanochannel to have a width no greater than about 100 nm.

10. The method of claim 6, wherein the insulator layer has a thickness of no greater than about 10 nm, and the gap is defined by the thickness of the insulator layer.

11. The method of claim 6, wherein the gap has a height measured between the first and second electrode layers, the height being in the range of about 0.3 nm to about 2 nm.

12. The method of claim 6, wherein the gap has a width, the gap width being greater than a width of the nanochannel.

13. The method of claim 6, further comprising covering the coating and electrodes with a polydimethylsiloxane (PDMS) material.

14. A method of DNA sequencing, comprising:
   providing a DNA sequencing device having a first layer, a nanochannel formed in the first layer, a pair of electrodes arranged vertically relative to each other and spaced apart to define an electrode gap, the electrode gap being exposed in the nanochannel, the electrode gap having a height measured between the pair of electrodes and a width, the height being in the range of about 0.3 nm to about 2 nm, the width being equal to or greater than a width of the nanochannel;

passing a DNA strand through the nanochannel and the gap;

detecting with the electrodes an electronic signal associated with individual nucleotides of the DNA strand as the DNA strand passes through the gap;

determining a sequence of the nucleotides based on the electronic signals.

15. The method of claim 14, wherein passing the DNA strand through the nanochannel and the gap includes moving the DNA strand using electrophoresis.

16. The method of claim 14, further comprising comparing the electronic signals to stored values for each nucleotide types.

17. The method of claim 14, wherein the DNA sequencing device further comprises a controller operable to receive the electronic signals and control operation of the electrodes.

18. The method of claim 14, further comprising displaying the DNA sequence on a display device.

* * * * *